United States Patent
Nunez et al.

(10) Patent No.: US 10,726,097 B2
(45) Date of Patent: Jul. 28, 2020

(54) READMISSION RISK SCORES

(71) Applicant: CareFusion 303, Inc., San Diego, CA (US)

(72) Inventors: Carlos Nunez, San Diego, CA (US); Ying Tabak, Weston, MA (US); Xiaowu Sun, Lincoln, RI (US); Vikas Gupta, Naperville, IL (US); Richard Johannes, Newton, MA (US)

(73) Assignee: CAREFUSION 303, INC., San Diego, CA (US)

( * ) Notice: Subject to any disclaimer, the term of this patent is extended or adjusted under 35 U.S.C. 154(b) by 345 days.

(21) Appl. No.: 15/295,639

(22) Filed: Oct. 17, 2016

(65) Prior Publication Data

US 2017/0109494 A1    Apr. 20, 2017

Related U.S. Application Data

(60) Provisional application No. 62/242,588, filed on Oct. 16, 2015.

(51) Int. Cl.
*G06F 19/00* (2018.01)
*G16H 50/20* (2018.01)
(Continued)

(52) U.S. Cl.
CPC ........... *G06F 19/325* (2013.01); *G16H 40/63* (2018.01); *G16H 50/20* (2018.01); *G16H 50/30* (2018.01)

(58) Field of Classification Search
USPC .......................................................... 705/3
See application file for complete search history.

(56) References Cited

U.S. PATENT DOCUMENTS 6,334,445 B1 * 1/2002 Mettinger ............ A61K 31/337
                                                      128/898
2006/0129427 A1 * 6/2006 Wennberg ............. G06F 19/328
                                                      705/2
(Continued)

FOREIGN PATENT DOCUMENTS

WO    WO-2013098740 A2 * 7/2013 ............. G06F 19/00

OTHER PUBLICATIONS

Amarasingham, Ruben et al., "Electronic medical record-based multicondition models to predict the risk of 30 day readmission or death among adult medicine patients: validation and comparison to existing models", BMC Medical Informatics & Decision Making, (2015) 15:39, DOI 10.1186/s12911-015-0162-6 (8 pages).

(Continued)

*Primary Examiner* — Linh Giang Le
(74) *Attorney, Agent, or Firm* — Morgan, Lewis & Bockius LLP

(57) ABSTRACT

Systems for use with a medical device for reducing medical facility readmission risks are provided. In one aspect, a system includes a medical device that is configurable with operating limit parameters for providing testing or treatment to a patient, and a limiting system. The limiting system includes a memory that includes patient-specific information for the patient and a database that includes readmission risk information, and a processor. The processor is configured to compare readmission risk parameters with the patient-specific information, and provide a readmission risk score for integration with medical devices and processes corresponding to the patient. Methods and machine-readable media are also provided.

20 Claims, 12 Drawing Sheets

(51) Int. Cl.
*G16H 40/63* (2018.01)
*G16H 50/30* (2018.01)

(56) References Cited

U.S. PATENT DOCUMENTS

| | | | | |
|---|---|---|---|---|
| 2011/0313788 A1* | 12/2011 | Amland | ............... | G06Q 50/22 |
| | | | | 705/3 |
| 2012/0276851 A1* | 11/2012 | Layne, IV | ............ | G06Q 20/32 |
| | | | | 455/41.2 |
| 2013/0191158 A1* | 7/2013 | Fillmore | ............... | G06F 19/00 |
| | | | | 705/3 |
| 2013/0262357 A1* | 10/2013 | Amarasingham | ...... | G16H 50/30 |
| | | | | 706/21 |
| 2015/0081328 A1 | 3/2015 | Tsui | | |

OTHER PUBLICATIONS

Donzé, Jacques, et al., "Potentially Avoidable 30-Day Hospital Readmissions in Medical Patients, Derivation and Validation of a Prediction Model", American Medical Association, Mar. 25, 2013 www.jamainternalmed.com, pp. E1-E7 (7 pages).

International Search Report and Written Opinion for Application No. PCT/US2016/057392, dated Dec. 22, 2016, 11 pages.

Tabak, Ying P. et al., "Development and Validation of a Disease-Specific Risk Adjustment System Using Automated Clinical Data", Health Research and Educational Trust, DOI: 10.1111/j.1475-6773. 2010.01126.x, Research Article, HSR: Health Services Research 45:6, Part I (Dec. 2010), pp. 1815-1835 (21 pages).

Tabak, Ying P., et al., "Using Automated Clinical Data for Risk Adjustment, Development and Validation of Six Disease-Specific Mortality Predictive Models for Pay-for-Performance", Medical Care, vol. 45, No. 8, Aug. 2007, pp. 789-805 (17 pages).

Tabak, Ying P., et al. "Using electronic health record data to develop inpatient mortality predictive model: Acute Laboratory Risk of Mortality Score (ALaRMS)", http://nrs.harvard.edu/urn-3:HUL. InstRepos:12152985, J Am Med Inform Assoc 2014, 21, pp. 455-463 (10 pages), doi:10.1136/amiajnl-2013-001790.

Van Walraven, Carl, et al., "Derivation and validation of an index to predict early death or unplanned readmission after discharge from hospital to the community", CMAJ 2010 Canadian Medical Association or its licensors, Apr. 6, 2010, 182(6), pp. 551-557 (7 pages).

* cited by examiner

300

| Variables | Derivation Cohort | | Validation Cohort | |
|---|---|---|---|---|
| | Discharges, n (column %) | Readmission, n (row %) | Discharges, n (column %) | Readmission, n (row %) |
| Total | 836,992 (100.0) | 99,386 (11.9) | 358,648 (100.0) | 42,825 (11.9) |
| Demographics (ALaRMS variables) | | | | |
| Age, years | | | | |
| <30 | 97,861 (11.7) | 4,652 (4.8) | 41,570 (11.6) | 1,967 (4.7) |
| 30-34 | 42,766 (5.1) | 2,220 (5.2) | 18,393 (5.1) | 936 (5.1) |
| 35-39 | 38,375 (4.6) | 2,656 (6.9) | 16,356 (4.6) | 1,106 (6.8) |
| 40-44 | 39,137 (4.7) | 3,720 (9.5) | 16,860 (4.7) | 1,610 (9.5) |
| 45-49 | 48,359 (5.8) | 4,993 (10.3) | 20,660 (5.8) | 2,127 (10.3) |
| 50-54 | 55,226 (6.6) | 6,039 (10.9) | 23,406 (6.5) | 2,653 (11.3) |
| 55-59 | 58,781 (7.0) | 7,096 (12.1) | 25,377 (7.1) | 3,015 (11.9) |
| 60-64 | 62,193 (7.4) | 8,119 (13.1) | 26,502 (7.4) | 3,549 (13.4) |
| 65-69 | 63,709 (7.6) | 8,641 (13.6) | 27,711 (7.7) | 3,759 (13.6) |
| 70-74 | 68,158 (8.1) | 9,689 (14.2) | 29,380 (8.2) | 4,194 (14.3) |
| 75-79 | 82,649 (9.9) | 12,545 (15.2) | 35,436 (9.9) | 5,366 (15.1) |
| 80-84 | 84,699 (10.1) | 13,490 (15.9) | 36,243 (10.1) | 5,783 (16.0) |
| 85-89 | 61,633 (7.4) | 10,193 (16.5) | 26,377 (7.4) | 4,461 (16.9) |
| >89 | 33,446 (4.0) | 5,333 (15.9) | 14,377 (4.0) | 2,299 (16.0) |
| Male | 333,362 (39.8) | 45,429 (13.6) | 142,368 (39.7) | 19,552 (13.7) |
| Admission laboratory test result (ALaRMS variables) | | | | |
| Albumin <= 2.4 g/dL | 22,182 (2.7) | 5,069 (22.9) | 9,527 (2.7) | 2,180 (22.9) |
| Albumin 2.5 - 2.7 g/dL | 22,280 (2.7) | 4,583 (20.6) | 9,585 (2.7) | 1,875 (19.6) |
| Albumin 2.8 - 3 g/dL | 39,678 (4.7) | 7,203 (18.2) | 17,008 (4.7) | 3,085 (18.1) |
| Albumin 3.1 - 3.3 g/dL | 57,962 (6.9) | 9,306 (16.1) | 24,837 (6.9) | 4,064 (16.4) |
| AST 31 - 40 U/L | 55,558 (6.6) | 8,156 (14.7) | 23,781 (6.6) | 3,496 (14.7) |
| AST 41 - 60 U/L | 36,898 (4.4) | 5,879 (15.9) | 15,632 (4.4) | 2,559 (16.4) |
| AST 61 - 100 U/L | 20,455 (2.4) | 3,406 (16.7) | 8,628 (2.4) | 1,489 (17.3) |
| AST > 100 U/L | 21,044 (2.5) | 3,100 (14.7) | 9,084 (2.5) | 1,417 (15.6) |
| Total Bilirubin 1.5 - 2 mg/dL | 15,857 (1.9) | 2,374 (15.0) | 6,735 (1.9) | 1,048 (15.6) |
| Total Bilirubin > 2.0 mg/dL | 14,697 (1.8) | 2,655 (18.1) | 6,350 (1.8) | 1,225 (19.3) |
| Calcium <= 7.9 mg/dL | 33,632 (4.0) | 5,520 (16.4) | 14,433 (4.0) | 2,448 (17.0) |
| Calcium 8 - 8.4 mg/dL | 78,666 (9.4) | 11,936 (15.2) | 33,423 (9.3) | 5,177 (15.5) |
| Calcium > 10.1 mg/dL | 33,872 (4.1) | 4,749 (14.0) | 14,631 (4.1) | 2,023 (13.8) |
| Creatinine > 2.0 mg/dL | 58,987 (7.1) | 13,593 (23.0) | 25,294 (7.1) | 5,852 (23.1) |
| pro BNP 8001 - 18000 pg/dL | 1,761 (0.2) | 401 (22.8) | 743 (0.2) | 204 (27.5) |
| pro BNP > 18000 pg/dL | 1,069 (0.1) | 275 (25.7) | 431 (0.1) | 105 (24.4) |
| BNP 1201 - 2400 pg/mL | 8,072 (1.0) | 1,844 (22.8) | 3,569 (1.0) | 811 (22.7) |
| BNP > 2400 pg/mL | 5,672 (0.7) | 1,387 (24.5) | 2,300 (0.6) | 603 (26.2) |
| Glucose <= 70 mg/dL | 1,1754 (1.4) | 1,996 (17.0) | 4,935 (1.4) | 902 (18.3) |

FIG. 3

| | | | | |
|---|---|---|---|---|
| Glucose 136 - 165 mg/dL | 96,757 (11.6) | 13,634 (14.1) | 41,719 (11.6) | 5,787 (13.9) |
| Glucose > 165 mg/dL | 121,390 (14.5) | 19,585 (16.1) | 51,877 (14.5) | 8,413 (16.2) |
| K <= 3.2 mEq/L | 37,439 (4.5) | 5,537 (14.8) | 16,170 (4.5) | 2,459 (15.2) |
| K 5 - 5.3 mEq/L | 26,881 (3.2) | 5,037 (18.7) | 11,469 (3.2) | 2,134 (18.6) |
| K > 5.3 mEq/L | 21,166 (2.5) | 4,559 (21.5) | 9,191 (2.6) | 1,989 (21.6) |
| Na <= 130 mEq/L | 33,078 (4.0) | 6,121 (18.5) | 14,036 (3.9) | 2,635 (18.8) |
| Na 131 - 135 mEq/L | 121,006 (14.5) | 18,679 (15.4) | 52,027 (14.5) | 8,012 (15.4) |
| Na 144 - 145 mEq/L | 21,770 (2.6) | 3,113 (14.3) | 9,423 (2.6) | 1,441 (15.3) |
| Na > 145 mEq/L | 11,157 (1.3) | 2,019 (18.1) | 4,741 (1.3) | 841 (17.7) |
| Alk Phos 116 - 220 U/L | 79,134 (9.5) | 13,960 (17.6) | 34,311 (9.6) | 6,249 (18.2) |
| Alk Phos 221 - 630 U/L | 16,415 (2.0) | 3,601 (21.9) | 6,955 (1.9) | 1,493 (21.5) |
| Alk Phos > 630 U/L | 1,989 (0.2) | 469 (23.6) | 841 (0.2) | 188 (22.4) |
| BUN 26 - 30 mg/dL | 49,162 (5.9) | 8,133 (16.5) | 20,713 (5.8) | 3,497 (16.9) |
| BUN 31 - 40 mg/dL | 51,513 (6.2) | 9,771 (19.0) | 22,162 (6.2) | 4,245 (19.2) |
| BUN 41 - 55 mg/dL | 33,809 (4.0) | 7,235 (21.4) | 14,305 (4.0) | 3,049 (21.3) |
| BUN > 55 mg/dL | 31,023 (3.7) | 7,240 (23.3) | 13,392 (3.7) | 3,052 (22.8) |
| pH Arterial <= 7.2 | 4,202 (0.5) | 618 (14.7) | 1,828 (0.5) | 284 (15.5) |
| pH Arterial 7.21 - 7.3 | 7,753 (0.9) | 1,287 (16.6) | 3,331 (0.9) | 559 (16.8) |
| pH Arterial 7.31 - 7.35 | 8,399 (1.0) | 1,378 (16.4) | 3,642 (1.0) | 644 (17.7) |
| pH Arterial > 7.48 | 4,870 (0.6) | 903 (18.5) | 2,095 (0.6) | 391 (18.7) |
| PO2 <= 50 mmHg | 4,175 (0.5) | 535 (12.8) | 1,830 (0.5) | 239 (13.1) |
| PO2 50.1 - 55 mmHg | 2,037 (0.2) | 361 (17.7) | 832 (0.2) | 143 (17.2) |
| PO2 >= 140.1 mmHg | 15,952 (1.9) | 2,464 (15.4) | 6,698 (1.9) | 1,045 (15.6) |
| pCO2 Arterial <= 35 mmHg | 18,703 (2.2) | 3,020 (16.1) | 8,123 (2.3) | 1,277 (15.7) |
| pCO2 Arterial >= 51 mmHg | 12,589 (1.5) | 2,394 (19.0) | 5,523 (1.5) | 1,101 (19.9) |
| PTT <= 22 | 9,761 (1.2) | 1,438 (14.7) | 4,284 (1.2) | 643 (15.0) |
| PTT 45.1 - 55 | 11,250 (1.3) | 2,140 (19.0) | 4,889 (1.4) | 885 (18.1) |
| PTT > 55 | 14,294 (1.7) | 2,483 (17.4) | 6,119 (1.7) | 1,058 (17.3) |
| PT INR 1.11 - 1.4 | 84,807 (10.1) | 14,079 (16.6) | 36,368 (10.1) | 6,074 (16.7) |
| PT INR 1.41 - 2 | 29,670 (3.5) | 5,554 (18.7) | 12,667 (3.5) | 2,404 (19.0) |
| PT INR 2.1 - 5 | 41,481 (5.0) | 7,559 (18.2) | 17,920 (5.0) | 3,294 (18.4) |
| PT INR > 5 | 6,005 (0.7) | 1,174 (19.6) | 2,618 (0.7) | 512 (19.6) |
| Bands 7 - 13% | 27,731 (3.3) | 4,135 (14.9) | 11,944 (3.3) | 1,714 (14.4) |
| Bands 14 -32% | 18,341 (2.2) | 2,773 (15.1) | 7,910 (2.2) | 1,143 (14.5) |
| Bands > 32% | 7,649 (0.9) | 1,019 (13.3) | 3,199 (0.9) | 449 (14.0) |
| Hemoglobin <= 10 g/dL | 87,775 (10.5) | 15,846 (18.1) | 37,840 (10.6) | 6,928 (18.3) |
| Hemoglobin > 18 g/dL | 2,099 (0.3) | 217 (10.3) | 986 (0.3) | 91 (9.2) |
| Platelets <= 115 10^9/L | 30,257 (3.6) | 6,143 (20.3) | 13,140 (3.7) | 2,780 (21.2) |
| Platelets 115.1 - 150 10^9/L | 47,704 (5.7) | 6,443 (13.5) | 20,783 (5.8) | 2,796 (13.5) |
| Platelets > 420 10^9/L | 38,561 (4.6) | 7,148 (18.5) | 16,443 (4.6) | 2,979 (18.1) |
| WBC <= 4.3 x1,000/mm$^3$ | 27,984 (3.3) | 5,339 (19.1) | 12,087 (3.4) | 2,361 (19.5) |

FIG. 4

| | | | | |
|---|---|---|---|---|
| WBC 11 - 14.1 x1,000/mm³ | 141,312 (16.9) | 15,795 (11.2) | 60,388 (16.8) | 6,747 (11.2) |
| WBC 14.2 - 19.8 x1,000/mm³ | 85,213 (10.2) | 10,478 (12.3) | 36,095 (10.1) | 4,302 (11.9) |
| WBC > 19.8 x1,000/mm³ | 28,494 (3.4) | 4,577 (16.1) | 12,109 (3.4) | 1,941 (16.0) |
| Troponin I 0.05-0.1 or CPK MB 3-5 ng/mL | 101,888 (12.2) | 16,007 (15.7) | 43,370 (12.1) | 6,863 (15.8) |
| Troponin I 0.11-0.2 or CPK MB 6-10 ng/mL | 29,352 (3.5) | 4,828 (16.4) | 12,710 (3.5) | 2,139 (16.8) |
| Troponin I 0.21-0.3 or CPK MB 11-34 ng/mL | 7,683 (0.9) | 1,328 (17.3) | 3,334 (0.9) | 552 (16.6) |
| Troponin I >0.3 or CPK MB >34 ng/mL | 17,576 (2.1) | 2,841 (16.2) | 7,480 (2.1) | 1,246 (16.7) |
| Number of discharges during previous 90 days | | | | |
| 0 | 673,214 (80.4) | 59,951 (8.9) | 288,330 (80.4) | 25,867 (9.0) |
| 1 | 118,160 (14.1) | 23,639 (20.0) | 50,777 (14.2) | 10,144 (20.0) |
| 2 | 31,653 (3.8) | 9,553 (30.2) | 13,527 (3.8) | 4,037 (29.8) |
| 3 | 9,471 (1.1) | 3,732 (39.4) | 4,073 (1.1) | 1,666 (40.9) |
| ≥4 | 4,494 (0.5) | 2,511 (55.9) | 1,941 (0.5) | 1,111 (57.2) |
| Additional information (from administrative data) | | | | |
| Race/Ethnicity | | | | |
| White | 683,564 (81.7) | 82,438 (12.1) | 292,977 (81.7) | 35,421 (12.1) |
| Black | 66,070 (7.9) | 8,155 (12.3) | 28,428 (7.9) | 3,546 (12.5) |
| Other | 87,358 (10.4) | 8,793 (10.1) | 37,243 (10.4) | 3,858 (10.4) |
| Payor | | | | |
| Medicare | 306,470 (36.6) | 47,584 (15.5) | 131,255 (36.6) | 20,495 (15.6) |
| Medicaid | 86,094 (10.3) | 8,117 (9.4) | 36,777 (10.3) | 3,622 (9.8) |
| Private or other | 444,428 (53.1) | 43,685 (9.8) | 190,616 (53.2) | 18,708 (9.8) |

Note:
ALaRMS: Acute Laboratory Risk of Mortality Score
AST: aspartate transaminase
Alkaline phos: alkaline phosphatase
BNP: brain natriuretic peptide
BUN: blood urea nitrogen
CPK MB: creatine phosphokinase MB
PCO2: partial pressure of carbon dioxide in arterial blood
PO2: partial pressure of oxygen in arterial blood
pro-BNP: pro-brain natriuretic peptide
PTT: partial thromboplastin time
PT INR: prothrombin time international normalized ratio
WBC: white blood cell count

FIG. 5

| Variable | Multivariable Adjusted Estimate | Multivariable Adjusted Odds Ratio (95% Confidence Interval) | RRS Risk Score |
|---|---|---|---|
| ALaRMS score | | | |
| 0-10 | Reference | | 0 |
| 11-20 | 0.43 | 1.53 (1.47, 1.60) | 1 |
| 21-30 | 0.74 | 2.10 (2.02, 2.17) | 2 |
| 31-40 | 1.00 | 2.72 (2.63, 2.81) | 2 |
| 41-50 | 1.27 | 3.55 (3.43, 3.67) | 3 |
| 51-60 | 1.47 | 4.34 (4.19, 4.49) | 3 |
| 61-70 | 1.57 | 4.82 (4.64, 5.01) | 4 |
| 71-80 | 1.56 | 4.78 (4.56, 5.00) | 4 |
| 81-90 | 1.56 | 4.78 (4.50, 5.07) | 4 |
| >90 | 1.46 | 4.31 (4.02, 4.62) | 3 |
| Number of discharges during previous 90 days | | | |
| 0 | Reference | | 0 |
| 1 | 0.73 | 2.08 (2.05, 2.12) | 2 |
| 2 | 1.23 | 3.43 (3.34, 3.52) | 3 |
| 3 | 1.65 | 5.20 (4.98, 5.43) | 4 |
| ≥4 | 2.42 | 11.20 (10.54, 11.90) | 6 |

Note: ALaRMS: Acute Laboratory Risk of Mortality Score; RRS: Early Readmission Risk Score; all $P$-value <0.0001.

| Model | Model Description (Groups of Variables in the Model) | C-Statistic |
|---|---|---|
| Models Using Electronic Health Record Data on Admission (Main Model) | | |
| I | ALaRMS (Acute Laboratory Risk of Mortality Score) | 0.646 |
| II | Model I + number of discharges during previous 90-day | 0.692 |
| Models with Additional Administrative Data (Main Model + Administrative Data) | | |
| III | Model II + Medicaid | 0.698 |
| IV | Model III + index hospital length of stay | 0.707 |
| V | Model IV + principal diagnosis-based clinical classification system (CCS) | 0.725 |
| VI | Model V + secondary diagnosis-based comorbidity score (CS) | 0.732 |

FIG. 7

| Variable | Discharges, n (%) | Readmission n (%) | Model c-statistic |
|---|---|---|---|
| Total | 1,195,640 (100.0) | 142,211 (11.9) | 0.697 |
| Subpopulation by Hospital Characteristics | | | |
| Teaching Status | | | |
| Non-teaching | 485,378 (40.6) | 56,820 (11.7) | 0.706 |
| Teaching | 710,262 (59.4) | 85,391 (12.0) | 0.692 |
| Urban/Rural Status | | | |
| Urban | 996,926 (83.4) | 119,464 (12.0) | 0.696 |
| Rural | 198,714 (16.6) | 22,747 (11.4) | 0.704 |
| Number of Beds | | | |
| ≤300 | 703,843 (58.9) | 84,809 (12.0) | 0.700 |
| >300 | 491,797 (41.1) | 57,402 (11.7) | 0.695 |
| Subpopulation by Type of Patients | | | |
| Medical versus Surgical Discharges | | | |
| Medical | 805,992 (67.4) | 109,312 (13.6) | 0.692 |
| Surgical | 389,648 (32.6) | 32,899 (8.4) | 0.690 |
| Clinical Classification System (CCS) Categories | | | |
| 1. Infectious and parasitic diseases | 29,968 (2.5) | 5,265 (17.6) | 0.641 |
| 2. Neoplasms | 65,135 (5.5) | 11,671 (17.9) | 0.681 |
| 3. Endocrine; nutritional; and metabolic diseases and immunity disorders | 43,565 (3.6) | 6,633 (15.2) | 0.677 |
| 4. Diseases of the blood and blood-forming organs | 10,539 (0.9) | 1,981 (18.8) | 0.665 |
| 5. Mental Illness | 19,820 (1.7) | 2,504 (12.6) | 0.673 |
| 6. Diseases of the nervous system and sense organs | 30,316 (2.5) | 3,316 (10.9) | 0.662 |
| 7. Diseases of the circulatory system | 280,387 (23.5) | 37,491 (13.4) | 0.655 |
| 8. Diseases of the respiratory system | 116,130 (9.7) | 18,970 (16.3) | 0.657 |
| 9. Diseases of the digestive system | 134,972 (11.3) | 16,838 (12.5) | 0.674 |
| 10. Diseases of the genitourinary system | 72,816 (6.1) | 8,632 (11.9) | 0.702 |
| 11. Complications of pregnancy; childbirth; and the puerperium | 147,510 (12.3) | 4,217 (2.9) | 0.581 |
| 12. Diseases of the skin and subcutaneous tissue | 24,567 (2.1) | 2,560 (10.4) | 0.694 |
| 13. Diseases of the musculoskeletal system and connective tissue | 80,684 (6.8) | 5,695 (7.1) | 0.653 |
| 14. Congenital anomalies | 1,675 (0.1) | 153 (9.1) | 0.619 |
| 16. Injury and poisoning | 104,248 (8.7) | 12,229 (11.7) | 0.668 |
| 17. Symptoms; signs; and ill-defined conditions and factors influencing health status | 29,579 (2.5) | 3,640 (12.3) | 0.676 |
| 18. Residual codes; unclassified; all E codes | 3,726 (0.3) | 416 (11.2) | 0.716 |

FIG. 8

READMISSION RISK SCORES

CROSS-REFERENCE TO RELATED APPLICATIONS

This application claims the benefit of priority from U.S. Provisional Application No. 62/242,588, filed Oct. 16, 2015, the entirety of which is incorporated herein by reference.

BACKGROUND

The present disclosure generally relates to reducing medical facility readmission risks, and more particularly to systems and methods for use with medical devices or medical systems for reducing medical facility readmission risks for previous or current patients.

SUMMARY

In accordance with various aspects of the present disclosure, a system is provided for reducing medical facility readmission risk, the system including a medical device that is configurable with operating parameters for providing one of testing and treatment to a patient and a medical control system. The medical control system includes a memory comprising patient-specific information for the patient and a readmission risk database comprising readmission risk parameters and a processor. The processor is configured to compare the patient-specific information for the patient with the readmission risk parameters; determine a readmission risk score for the patient; receive a patient protocol based on decision support provided by the determined readmission risk score; and provide a configuration of the operating parameters of the medical device for providing the one of testing and treatment to the patient based on the received patient protocol.

In accordance with other aspects, a method for use with a medical device for reducing medical facility readmission risk, the method including: determining patient-specific information for a patient; comparing the patient-specific information for the patient with a database of readmission risk parameters; determining a readmission risk score for the patient; determining a patient protocol for the patient based on decision support provided by the determined readmission risk score; configuring, by a processor of the medical device, operating parameters of the medical device for providing one of testing and treatment to the patient based on the determined patient protocol; and displaying, by the medical device, an indication that the operating parameters of the medical device have been configured based on the determined patient protocol, the notification comprising information regarding the configured operating parameters.

In accordance with other aspects, a non-transitory machine-readable medium is provided that embodies instructions that, when executed by a machine, cause the machine to perform a method for determining a readmission risk score. The method includes receiving patient-specific information for a patient; comparing the received patient-specific information for the patient with a database of readmission risk parameters; determining a readmission risk score for the patient; storing the patient's determined readmission risk score; determining a patient protocol for the patient based on decision support provided by the stored readmission risk score; configuring, by the machine, operating parameters of the medical device for providing one of testing and treatment to the patient based on the determined patient protocol; and displaying, by the medical device, an indication that the operating parameters of the medical device have been configured based on the determined patient protocol, the notification comprising information regarding the configured operating parameters.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 3-5 illustrate an example table of patient characteristics by derivation and validation cohort.

FIG. 7 illustrates an example table of cumulative c-statistic of readmission models.

FIG. 8 illustrates an example table of sensitivity analysis.

DETAILED DESCRIPTION

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. In the referenced drawings, like numbered elements are the same or essentially similar. Reference numbers may have letter suffixes appended to indicate separate instances of a common element while being referred to generically by the same number without a suffix letter.

The present disclosure provides a system that evaluates patient-specific data, such as a patient's previous or current hospital admission and/or discharge data, laboratory results or characteristics (e.g., age, gender, medical history), in order to determine the patient's medical facility (e.g., hospital, clinic) readmission risk score (RRS). The patient's RRS may be integrated with medical devices and medical systems for providing decision support for current and future care to the patient. For example, providing a patient's RRS provides a capability to notify a clinician of scenarios to prevent or minimize future hospital readmission for the patient. As another example, a patient's RRS may provide decision support for a clinician or caregiver to determine a patient protocol for testing or treatment that may minimize future hospital readmission for the patient. Furthermore, incorporation of a patient's RRS can assist clinicians in monitoring and intervening in situations related to appropriate methods of administering laboratory tests, dispensing medications, providing infusion or respiratory services. The present disclosure also provides for verifying that the right testing and treatment, based on data specific to the right patient, has been given in the right manner, in the right amount, and at the right time to minimize the risk of hospital readmission.

Figure 1:
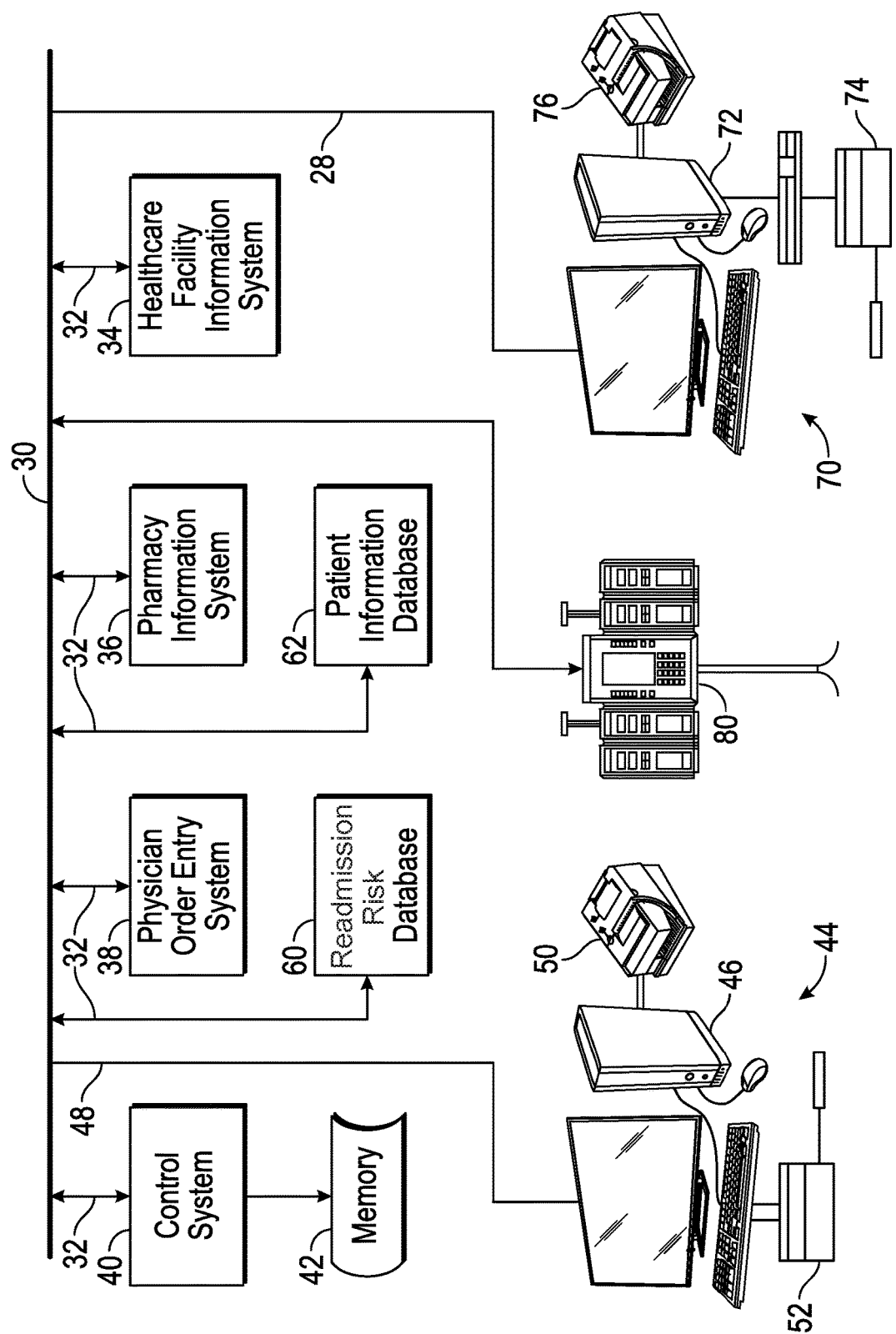
FIG. 1 is a block diagram and graphical representation of a care management system for reducing medical facility readmission risks.

Referring now to the drawings, FIG. 1 provides an example illustration of an integrated healthcare facility-wide information and care management system 28 in accordance with certain aspects of the present disclosure. Various subsystems of a healthcare facility's information management system are connected together by way of a facility communication system 30. The communication system 30 may include, for example, any one or more of a personal area network (PAN), a local area network (LAN), a campus area network (CAN), a metropolitan area network (MAN), a wide area network (WAN), a broadband network (BBN), the Internet, and the like. Further, the communication system 30 can include, but is not limited to, any one or more of the following network topologies, including a bus network, a star network, a ring network, a mesh network, a star-bus network, tree or hierarchical network, and the like. As shown in FIG. 1, the communication system 30 connects through various interfaces 32 to a healthcare facility information system 34, a pharmacy information system 36, a patient information database 62, a physician order entry system 38, a readmission risk database 60, and a control system 40 (or "limiting system").

The facility communication system 30 is not meant to be taken in a limited sense. Such a facility communication system 30 may encompass an entire healthcare facility or may be located only in a small area of the healthcare facility. It may also include a communication system in a healthcare facility other than a hospital (e.g., outpatient clinic) and may have application to an alternate care facility, such as a patient's home. Additionally, the word caregiver is intended to be used in its broadest sense and is meant to include nurses, physicians, health care specialists, and others who provide care to patients.

The control system 40 in accordance with an aspect of the present disclosure may be, for example, a server or other computer having sufficient memory 42 and processing capability to connect with the communication system 30 and configure a medical device 80. The control system 40 includes operational software or other instructions for carrying out various aspects of the present disclosure, as will be discussed more fully below, enabling communications with other hardware or networks, and data input and output and report generation and printing, among other functions. While the control system 40 is shown as a separate piece of equipment, it will be understood that the control system 40 and the associated memory 42 may also be incorporated into another element, such as the medical device 80. The medical device 80 may include a communication device 82 used to provide communications between the medical device and the control system 40. Various forms of such a communication device 82 may be used, such as wired or wireless communication.

The communication system 30 may comprise, for example, a wired or wireless Ethernet (IEEE 522.3) utilizing transmitters and receivers positioned throughout the healthcare facility and/or attached to various computers, clinical devices and other equipment used in the facility. In such a wireless system, the signals transmitted and received by the system could be radio frequency (RF), infrared (IR), or other means capable of carrying information in a wireless manner between devices having appropriate transmitters or receivers may be used. It will be immediately understood by those skilled in the art that such a system may be identical to the system set forth in FIG. 1, with the exception that no wires are required to interconnect the various aspects of the system.

A caregiver station 44 will typically include a terminal or computer system 46 connected either directly or through an interface 48 to the communication system 30, allowing users at the nurse station to enter and retrieve patient data or information from other systems, such as the healthcare facility information system 34, the pharmacy information system 36, the physician order entry system 38, or other systems used in the facility. It should be understood that not all users will be provided with access rights to each system. For example, physicians may be able to access the physician order entry system 38 from the caregiver station system 44 to enter, edit, or track medication orders, but a caregiver may only be able to view such orders. Moreover, while the present disclosure is described with reference to the computer system 46 being located at a caregiver station 44, the computer system 46 may also be a satellite system that is located anywhere in the care-giving facility where it is convenient or efficient to do so. Such a satellite computer system may be operably connected to the communication system 30 using either a wired or wireless network connection. A printer 50 may also be connected to the n computer system 46 for printing reports, bar codes, labels, or other materials, and a bar code reader 52 may be provided for reading bar codes on medication labels, reports, or other items having bar coded labels provided for identification. In one or more embodiments where radio frequency identification (RFID) tags are used with medications, patients, equipment, or in other ways, the caregiver station 44 may also include an interrogator or RFID reader (not shown) for use with the RFID tags.

Patient stations 70 having a computer 72 may be located at patient bedsides in a healthcare facility. Such stations 70 may serve a single patient, or may serve more than one patient, depending on the design and arrangement of the patient area. There may also be a variety of equipment or clinical devices attached to the bedside computer 72. Examples of such devices are a bar code reader 74, a printer 76, patient monitoring equipment (not shown) for monitoring patient vital signs, or other patient-specific assets (e.g., medical devices) assigned to the patient. Other infusion, respiratory or drug delivery devices and/or patient monitoring equipment such as cardiac or respiratory monitors may also comprise or form a part of the medical device.

The bedside equipment and clinical devices are typically equipped with data communication technology such as RS 232 serial ports or proprietary communication ports that allow information and data to be communicated to and from the equipment or clinical device. Using this communication technology, the bedside equipment and clinical devices may be connected to the bedside computer 72, or, alternatively, they may be connected, either by wire or wireless system, to the facility communication system 30. Wireless technology, such as RF, infrared (IR), or other wireless communication protocols, may be used, and wired technology establishing a local area network (LAN), Ethernet, or others may be used.

In accordance with aspects of the present disclosure, readmission risk database 60 stores information that is provided to determine a static and/or dynamic hospital readmission risk score for a previous or current patient. Various types of information may be stored in the memory of the readmission risk database 60, including data bases containing information about demographics, laboratory test results, prior hospital/clinic discharge data, Medicare/Medicaid data, index hospital length of stay, principal diagnosis-based clinical classification data, and secondary diagnosis-based comorbidity scores. For example, readmission risk database 60 data may be combined in different ways to determine a static RRS for a patient upon admission to a hospital. The static RRS may then be integrated with laboratory devices, medicine dispensing devices, and respiratory or infusion devices used in the ongoing care of the patient. As another example, the readmission risk database 60 data may be continuously refined to revise the initial RRS, thus providing a dynamic RRS for the patient. Here, the patient's initial RRS may be dynamically revised based on laboratory results or treatment protocols the patient has just received. The term database as used herein will be understood by those skilled in the art to be used as is commonly understood. That is, the term database refers to a collection of values or information organized, formatted, and stored in such a manner as to be capable of being retrieved and analyzed using an appropriate program contained in software or other form.

In one or more embodiments of the present disclosure, the readmission risk database 60 may be interfaced to the caregiver station computer system 46 or any other of the information systems of the central system of an institution through a cradle or other docking device that provides a connection between the readmission risk database 60 and the computer system 46. In this embodiment, use of the cradle allows information to flow between the readmission risk database 60 and the nurse computer system 46. This information may then be processed and stored on the computer system 46, or the information may be communicated by the computer system 46 through the interface 48 to various other facility information systems over the communication system 30. In this manner, information from the pharmacy information system 30, for example, may be communicated through the communication system 30, the caregiver station 44 computer system 46, and to the readmission risk database 60. Similarly, information contained within the readmission risk database 60 may be communicated through the caregiver station computer system 46, the interface 48, and the communication system 30 to any of the interconnected systems 34, 36, 38, 40, or 62.

The readmission risk database 60 may be stored on a device, such as a server. The healthcare facility may also or alternatively have the readmission risk database 60 centrally located in the memory 42 of the control system 40. The readmission risk database 60 may be centralized on one server, spread out over multiple servers and/or devices, or cloud based with access by an authorized portal, for example. The readmission risk database 60 may have a storage capability and technology for interfacing with a computer system or network so that information may be communicated between the readmission risk database 60 and other devices, such as computers, medication administration devices, clinical devices such as vital signs monitoring devices and the like.

In accordance with aspects of the present disclosure, the control system 40 is configured to obtain patient-specific information from the patient information database 62, a patient RRS from the readmission risk database 60, and device information from the medical device 80. The patient information database 62 may itself obtain and store patient-specific information retrieved from the physician order entry system 38, the pharmacy information system 36, and the healthcare facility information system 34. In certain aspects, information may be retrieved from the medical device 80 prior to actual use with the patient, and the control system 40 can retrieve, evaluate and or determine the patient RRS from the readmission risk database 60 in view of the patient-specific information for the patient associated with the medical device 80 to determine if testing or treatment protocols using the medical device 80 fall within institutionally established guidelines for decreasing the risk of hospital readmission for the patient.

If the RRS indicates that the parameters or information entered into the medical device 80 are appropriate in that they fall within the established guidelines, then an indication to that effect may be provided to the caregiver and the caregiver may then begin testing or administrating treatment. If the RRS indicates that one or more parameters or information do not meet the established guidelines, a warning or alert may be provided to the caregiver to provide alternate or revised testing or treatment protocols. In one or more embodiments, the medical device 80 may be automatically inhibited from starting administration of a test, a medication or a treatment unless it receives a signal from the control system 40 that the comparison was favorable, thus providing a fail-safe against testing or treatment that does not minimize the risk of hospital readmission for the patient.

In certain aspects, information may be retrieved information from the medical device 80 after actual testing or treatment begins, and the control system 40 can evaluate the information from the readmission risk database 60 in view of the patient-specific information for the patient associated with the medical device 80 to determine if the parameters currently being used by the medical device 80 fall within institutionally established guidelines for the administration of a particular test or treatment. For instance, the evaluation for a test/treatment being administered may occur during administration of the test/treatment, such as when, for example, testing parameters are adjusted to add or change the testing protocol or doses are adjusted to maintain blood pressure or heart rate or blood sugar levels. Errors may then be prevented and advisories posted at any point during the test/treatment administration.

The control system 40 is capable of retrieving testing or medication administration parameters or information from a medical device 80, and storing data or information concerning various transactions in its memory 42 representing the identity and testing/treatment regimens given to a patient, as well as other information, such as caregiver identity, equipment location, patient vital signs information, or any other information sought to be recorded. The control system 40 may also store data or information concerning primary or secondary validation of previous and/or duplicate transactions of testing or medical treatment information. The control system 40 may also provide, for display, messages or other information to a caregiver, such as warnings or prompts to enter data, related to testing or medication administration. Moreover, information entry means of the control system 40 may be used for manually entering information into the control system 40 for storage in the memory 42 of the control system 40. In certain aspects, the control system 40 may store information in memory 42 representing patient specific tests/treatments spanning multiple protocols or hospitalizations. For example, the control system 40 may identify and track how a patient's RRS dynamically changes based on testing or treatment protocols administered to the patient. As another example, the control system 40 may identify and track how a specific patient's RRS correlates with the RRS of other patients or groups of patients.

While specific examples of a control system 40 are set forth herein, it will be understood that the control system 40 is meant to include any device that carries out the basic concept of the disclosure. That is, a device that receives testing or treatment information from a medical device, such as, for example, but not limited to, laboratory test equipment (e.g., X-Ray machines, CT scanners, PET scanners, blood testing equipment), an infusion pump, respiratory therapy device or other instrument which performs similar functions, a medication dispensing device, receives information specific to one or many patients, and has a processor capable of comparing the received information to institutionally established testing or treatment guidelines or other pertinent information or data, such as previous hospital discharge data, and then providing an indication of the result of the comparison to a caregiver before administration of a test or treatment to a patient is begun, will accomplish the aims of the present disclosure. A particularly advantageous embodiment includes storing information about the patient, such as the testing administration or treatment parameters, and/or other information, such as the identity of the patient and caregiver, in the memory of the readmission risk database 60 until the readmission risk database 60 re-establishes a communication connection with the control system 40, whereby the information stored in the memory of the readmission risk database 60 may be communicated to the control system 40 and incorporated into one or more of an institution's information databases. Similarly, information about the patient's care, such as the testing administration or treatment parameters, and/or other information, such as the identity of the patient and caregiver, may be stored in the memory of the medical device 80 until, for example, the medical device 80 re-establishes a communication connection with the control system 40. Updating the databases provides a verification that the test/treatment has been rendered, thereby avoiding a duplicate test/treatment. In this manner, the present disclosure "closes the loop" ensuring that the optimal testing or treatment protocol are provided to the patient to minimize risk of hospital readmission.

Figure 2:
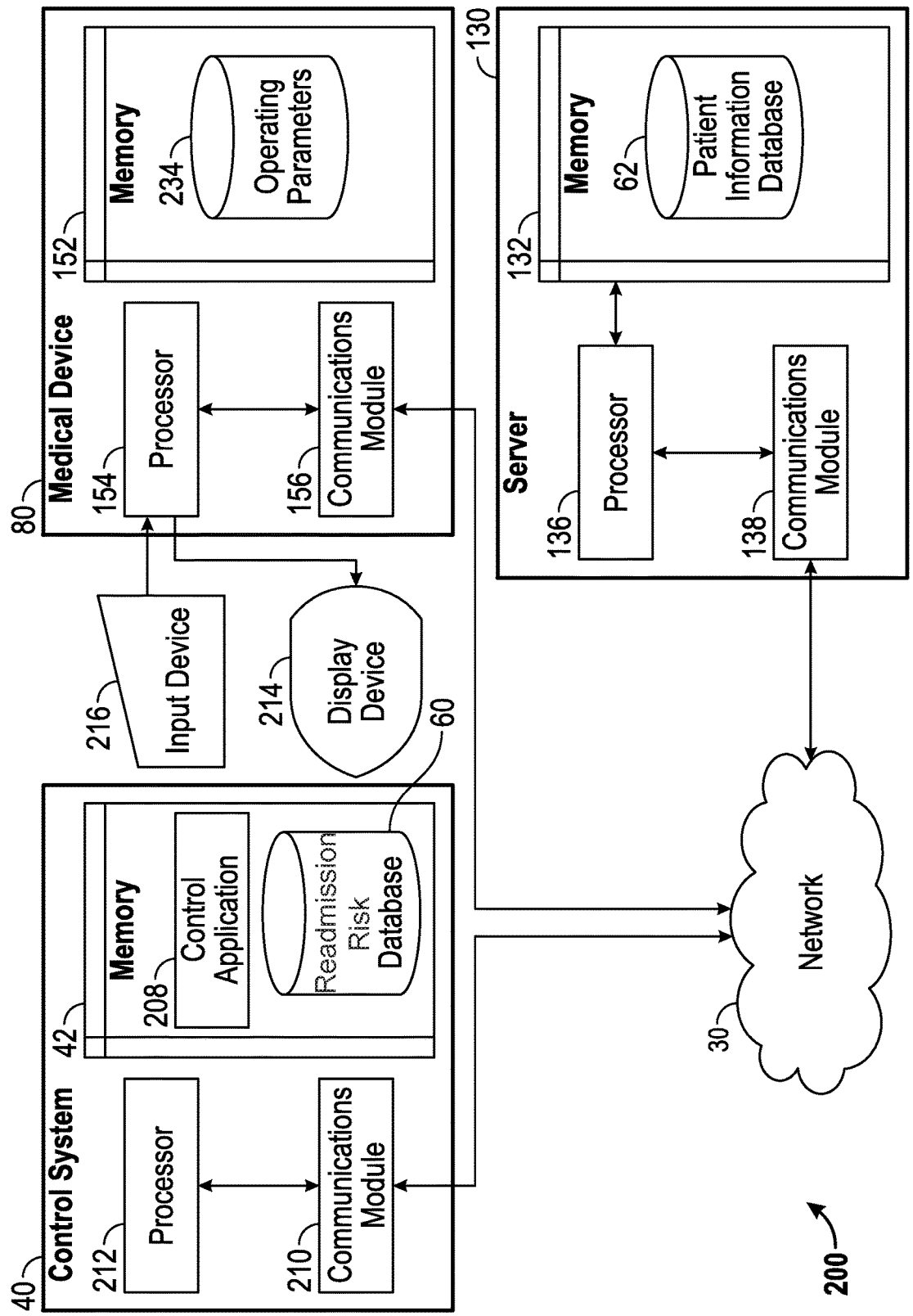
FIG. 2 is a block diagram illustrating an example control system, server, and medical device from the architecture of FIG. 1 according to certain aspects of the disclosure.

FIG. 2 is a block diagram 200 illustrating an example control system 40 (or "limiting system"), medical device 80, and server 130 from the architecture of FIG. 1 according to certain aspects of the disclosure. The control system 40, the medical device 80, and the server 130 are connected over the network 30 via respective communications modules 210, 156, and 138. The communications modules 210, 156, and 138 are configured to interface with the network 30 to send and receive information, such as data, requests, responses, and commands to other devices on the network. The communications modules 210, 156, and 138 can be, for example, modems or Ethernet cards and communicate over a wired or wireless connection.

The control system 40 includes a processor 212, the communications module 210, and a memory 42 that includes a control application 208 and a readmission risk database 60. The readmission risk database 60 includes patient information for determining a patient RRS and providing testing/treatment to a patient using the medical device 80. The medical device 80 is configurable with operating limit parameters for providing testing, treatment and/or medication to a patient. The medical device 80 can be, for example, laboratory equipment, an infusion pump, a ventilator or a medication dispensing system. The medical device 80 includes an input device 216, such as a keypad, for manual entry of operating parameters 234 (e.g., X-Ray dosing limits, medication dosing limits), as well as a display device 214, such as a monitor, for notifications and confirmation of entered operating parameters 234.

The processor 212 of the control system 40 is configured to execute instructions, such as instructions physically coded into the processor 212, instructions received from software in memory 42, or a combination of both. For example, the processor 212 of the control system 40 executes instructions to receive patient-specific information for a patient from a patient information database 62 stored in a memory 132 of a server 130. The patient-specific information can be received from an external data system (e.g., server 130) in a native message format of the external data system, and the processor 212 of the control system 40 can be configured to convert the patient-specific information into an internal messaging format configured for use with the control system 40. The processor 212 can be configured to perform the conversion according to the system and method of converting messages being sent between data systems using different communication protocols and message structures described in U.S. patent application Ser. No. 13/421,776, entitled "Scalable Communication System," and filed on Mar. 15, 2012, the disclosure of which is hereby incorporated by reference in its entirety for all purposes. The memory 42 of the control system 40 can include, for example, an interface module for communicating with the server 130. The interface module can include information on the communication protocol and data structure used by the server 130 and is configured to both receive messages from and transmit messages to the server 130.

The processor 136 of the server 130 is configured to collect and store in the patient information database 62 patient-specific information from the physician order entry system 38, pharmacy information system 36, and healthcare facility information system 34 over the network 30. In certain aspects, the patient information database 62 can be stored in the memory 42 of the control system 40. The patient-specific information includes, for example, laboratory data for a patient. The laboratory data can include a blood coagulation measure, a vitamin level, a platelet count value, a thromboplastin time, or a serum level for a patient. The patient-specific information can also include a medication ordered for the patient, a time at which the medication is ordered for the patient, a treatment plan for the patient, a medication resistance of the patient, a weight of the patient, a height of the patient, a body surface area of the patient, an age of the patient, a gender of the patient, or an ethnicity of the patient.

The processor 212 of the control system 40 may be configured to compare the patient information in the readmission risk database 60 with the patient-specific information from the patient information database 62, and provide a modification (e.g., by instructing a processor 143 of the medical device 80) the operating parameters 234 in the memory 152 of the medical device 80 for providing the testing/treatment to the patient based on a determination of the patient's RRS. The modified operating parameters 234 can be provided for display on the display device 214 of the medical device 80, or can automatically be implemented in the operating parameters 234 of the medical device 80.

In certain aspects, the processor 212 of the control system 40 is configured to provide a notification to the medical device 80 indicating that the operating parameters 234 for providing the testing/treatment to the patient have been modified based on the RRS from the readmission risk database 60. For example, the processor 212 of the control system 40 can instruct the processor 154 of the medical device 80 to display an alert with operating parameters 234 that have been modified by the control system 40 based on patient-specific information and the readmission risk database 60. The display can be seen by a clinician near the medical device 80. In certain aspects, the processor 212 is further configured to receive an input from a caregiver to override the modification of the operating parameters 234. Thus, the caregiver can override the modification provided by the control system 40 by using the input device 216 of the medical device 80. In addition to a confirmation to override the modified operating parameters, the caregiver can also be required to provide a reason why the caregiver has overrode the modification of the operating parameters 234. The processor is configured to record when the caregiver overrides the modification of the operating parameters 234, such as in the memory 42 of the control system 40.

In certain aspects where the processor 212 of the control system 40 is configured to provide a notification to the medical device 80, the processor 212 is configured to receive configuration parameters for determining whether to provide the notification based on an identity of a caregiver, identification of a location of the medical device, or an institutional preference. For example, the processor 212 can configure the medical device 80 to require a confirmation step for operating parameters 234 that exceed high limit warnings (e.g., a maximum amount for a medication dose), but not for low limit warnings (e.g., a minimum amount for the medication dose). As another example, the processor 212 can configure the medical device 80 to require a confirmation step for certain laboratory tests, or for a first time a laboratory test is provided to a patient using the medical device 80. The configuration for when to display an alert and for what reasons can be set by an institution in which the medical device 80 is located.

As yet another example, the processor 212 can configure the medical device 80 to display alerts and/or require a confirmation step based on a care area in which the medical device 80 is located or by the caregiver associated with the medical device. For instance, in an operating room, the operating parameters 234 for providing a medication are usually very different than the operating parameters 234 for providing a medication to a patient in a pediatric ward. The operating parameters 234 of the medical device 80 can be configured or otherwise modified by the control system 40 accordingly. As another example, if a caregiver associated with a medical device 80 is highly trained with over 10 years of experience, then an alert may not be displayed to the caregiver as compared to another caregiver with limited experience.

Turning to FIGS. 3-10, a discussion of readmission risk and determination of an RSS is provided. Readmission shortly after discharge is associated with clinical and financial burden to patients and society. It is used as a publicly reported metric with reimbursement implications to hospitals by the Centers for Medicare and Medicaid Services (CMS). For hospitals with excess risk-standardized readmission rates, CMS started lowering the reimbursement in FY2013. As of FY2015, the penalty is up to 3% lower reimbursement for certain clinical conditions (acute myocardial infarction [AMI], heart failure [HF], pneumonia, chronic obstructive pulmonary disease, total hip arthroplasty, and total knee arthroplasty).

Many factors may be associated with readmissions. Some may be intrinsic, attributable to the reduced reserves of patients due to disease progression and severity at each admission. Some factors may relate to the clinical planning and care coordination while patients are still in the hospital. Some factors may relate to post-discharge care and other social factors.

Typical readmission risk adjustment models mostly rely on administrative data submitted to the payers after patients are discharged. Models relying on administrative data cannot be applied to the real-time patient care environment because the discharge diagnoses are not available until after patients are discharged. Typical existing models incorporate variables for comorbidity based on secondary diagnoses and use of prior medical services, but lack clinical data to assess the impact of physiological function or acute illness severity. The limited number of studies that attempted to incorporate physiological variables focused on early prediction of readmission risk of a predefined clinical condition such as congestive heart failure. Such disease-specific predictive models have applied value when the electronic health record (EHR) system is highly advanced and able to correctly classify patients into specific disease groups. However, unlike discharge diagnoses that are standardized using codes from the International Classification of Diseases, 9th Revision, Clinical Modification (ICD-9-CM), admission diagnoses are not standardized across U.S. hospitals. Very often at the time of admission, patients display multiple signs and symptoms suggesting more than one clinical condition, which makes it difficult to unambiguously classify them into a single clinical category.

From a hospital comparison perspective, while it is helpful to assess readmission rates for specific groups of patients, these conditions account for only a small minority of total readmissions. According to the nationally representative data reported by the Agency for Healthcare Research and Quality (AHRQ), the 30-day all cause readmission volume of AMI, HF, and pneumonia in 2012 accounted for approximately 9.8% of total readmission volume. Further, the CMS has begun exploring hospital-wide (all-condition) 30-day risk-standardized readmission measure and risk adjustment models. Hence, understanding the full picture of hospital readmission may have practical implications to hospitals and the government agency.

As an example towards such understanding, a study was performed wherein the objective was two-fold. First, developing an early readmission risk score (RRS) for all hospitalized adult patients, using clinical data at the time of admission that were captured in the EHR systems. Second, expanding the early RRS model to include administrative data (e.g. discharge diagnoses) that are available after patients are discharged. One example may be that clinical severity and frequency of recent hospital stays (captured in the real-time EHR system) increase the risk of readmission. Another example may be that type of diseases and comorbidities captured in the administrative data may enhance the predictive accuracy. For applications, the early RRS may serve as a potential real-time decision support tool for clinicians to target high risk patients for discharge planning or other potential readmission preventive interventions. The administrative data enhanced post-discharge model may be used for retrospective inter-hospital comparison of risk adjusted readmission rates.

An example database is one of the Clinical Research Databases from CareFusion-BD (San Diego, Calif. [formerly CareFusion/Cardinal Health/MediQual]). This database has been used for research for the past two decades and the data collection system has been fully described elsewhere. In this example, data was used from the EHR systems of 70 acute care hospitals for all consecutively hospitalized adult patients (age 18 years or older) from 2006 through 2008. The laboratory data included numeric laboratory test results and collection time. A total of 95% of patients had laboratory data on the day of admission. For patients with multiple laboratory assessments on the admission day, the first reported value was used. For patients who did not have laboratory data on admission day, the laboratory data on the next day were used. The database also included imported hospital administrative data comprising demographics, admission and discharge date, discharge disposition, principal diagnosis, and secondary diagnosis codes.

In the present example, the outcome variable was all-cause readmission within 30 days from index hospital discharge. A patient could have multiple admissions during the study period. The analytic unit was the inpatient admission episode.

For the first model (early RRS), the candidate variables were restricted to information in the EHR system that were widely available at or soon after the hospital admission in order to generate a predictive model applicable shortly after patients were hospitalized. Here, a published Acute Laboratory Risk of Mortality Score (ALaRMS) was used as an aggregated measure of clinical severity. ALaRMS assesses the clinical severity of hospitalized patients using demographics and admission laboratory test results. It included weighted age, gender, and a total of 23 numeric laboratory test results: serum chemistry (alphabetically ordered: albumin, aspartate transaminase[AST], alkaline phosphatase, blood urea nitrogen [BUN], calcium, creatinine, glucose, potassium [K], sodium [Na], and total bilirubin); hematology and coagulation parameters (bands, hemoglobin, partial thromboplastin time [PTT], prothrombin time international normalized ratio [PT INR], platelets, and white blood cell count [WBC]); arterial blood gas (partial pressure of carbon dioxide [PCO2], partial pressure of oxygen [PO2], and pH value); cardiac markers (brain natriuretic peptide [BNP], creatine phosphokinase MB [CPK MB], pro-brain natriuretic peptide [Pro-BNP], and troponin I).

The numbers of admissions in the previous 90 days were included as the second dimension of readmission risk. The rationale is that both progression of disease and increasing severity of disease reduces patients' intrinsic reserve. The more frequent hospitalization, the more likely they will be readmitted. This variable also takes into account the nature of many chronic illnesses that can be managed but not necessarily cured. Hence, a certain rate of readmission may be expected. This notion is also corroborated with the findings that the healthcare expenditure for the final year of life accounts for approximately $40,000 per Medicare decedent, and the 5% of Medicare patients who die each year account for nearly 30% of payments.

In a second model (administrative data enhanced post-discharge model), in addition to the RRS, the Medicaid status was tested as a surrogate for low social economic status, length of stay, and discharge diagnoses of index hospital discharge. Here, the AHRQ's principal diagnosis-based Clinical Classifications Software (CCS) and secondary diagnosis-based Comorbidity Software (CS) were used as standard disease classification tools. The CCS collapses over 14,000 ICD-9-CM diagnosis codes into 285 clinically meaningful categories. The CS grouped selected secondary diagnosis codes into 30 comorbidity categories.

In this example, as shown in FIGS. 3-5, a results table 300 shows that the study population was randomly split into 70% as the derivation cohort 310 and 30% as the validation cohort 320. To derive the early readmission risk model, the relationship of the ALaRMS score (the aggregated clinical severity) and the readmission rate were first examined and categorized. Similarly, the number of inpatient discharges during the 90 days prior to the index discharge and the readmission rate were examined and categorized. The final model was converted to an integer score system (early readmission risk score [RRS]) using a method described in the Framingham Study. Specifically, the variable with the smallest coefficient in the final multivariable model was identified and applied as the denominator. Then each of the remaining regression coefficients in the model was divided by this denominator and the resulting quotient was rounded to the nearest whole number (integer), which formed the score weight for that variable. Each person's overall readmission risk score was calculated by summing the points across all variables present. Converting model coefficients into a score system makes the risk adjustment model easy to understand and implement. The RRS was validated using the validation cohort 320. Model discrimination was assessed using the c-statistic and the 95% confidence intervals (CI) were estimated using 1,000 bootstrap simulations. The bootstrap process randomly samples with replacement the study cohort. It fits the model and generates the c-statistic for each random sample. The 2.5th and 97.5th percentiles were used as the lower and upper limits of c-statistic 95% CI.

For the post-discharge model, candidate variables available after discharge were added, including admission source, index hospital length of stay (LOS), principal diagnosis-based CCS, and secondary diagnosis-based CS. The value $p<0.05$ was used as the model variable retention criterion. The c-statistic change was examined when each group of variables was added to the model. Sensitivity analysis was conducted to assess the predictive accuracy (c-statistic) of the RRS when applied to patients by different type of hospital characteristics (teaching status, number of beds, rural versus urban) as well as patient categories (medical versus surgical and discharge principal diagnosis-based disease categories).

For this example, for the derivation cohort 310, there were 836,992 discharges, and 99,386 (11.9%) readmissions (FIGS. 3-5). There were 39.8% male. White accounted for 81.7% of total discharges. Medicare accounted for 36.6%. The overall median age was 63 years, interquartile range (IQR) was 43, 78. The admission laboratory test results showed that patients with abnormal results had higher readmission rates. The number of discharges during the previous 90 days was associated with the readmission rate in a graded fashion. The patient characteristics for the validation cohort 320 were similar.

Figure 6:
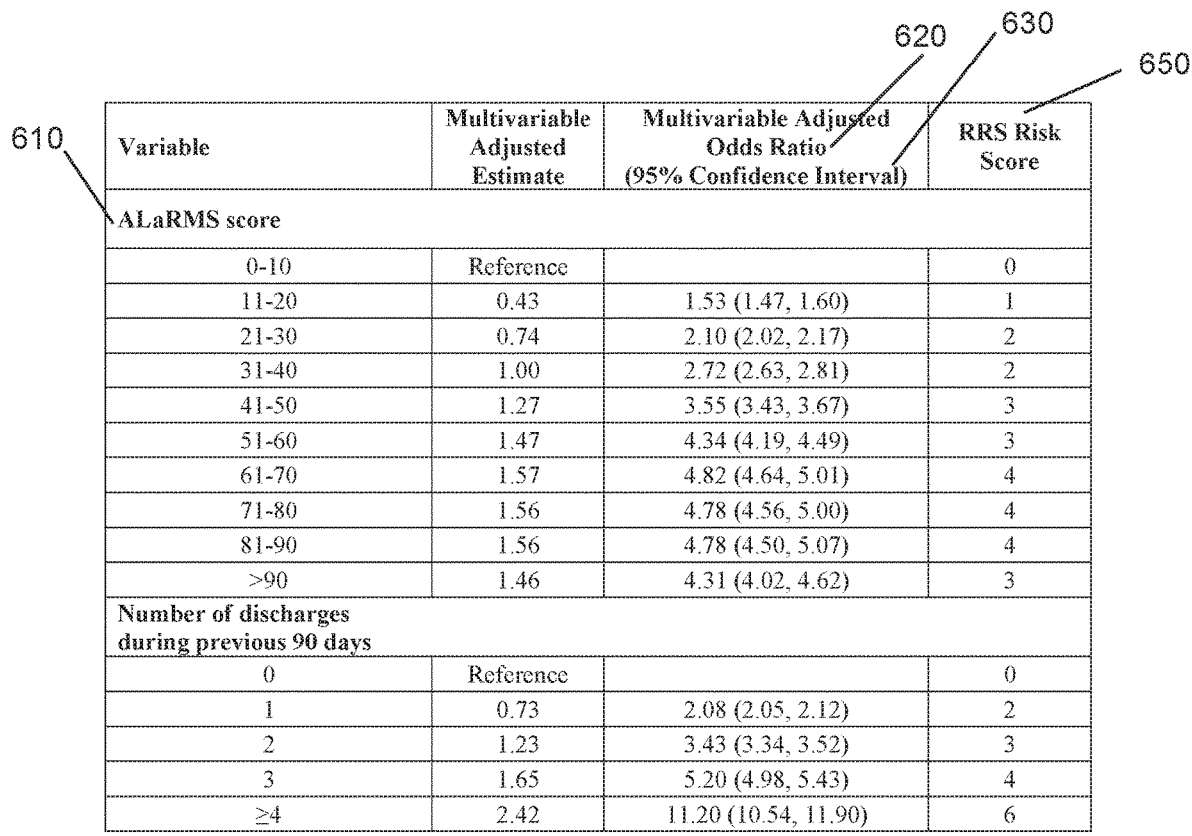
FIG. 6 illustrates an example table of early readmission model and risk score.
Figure 9:
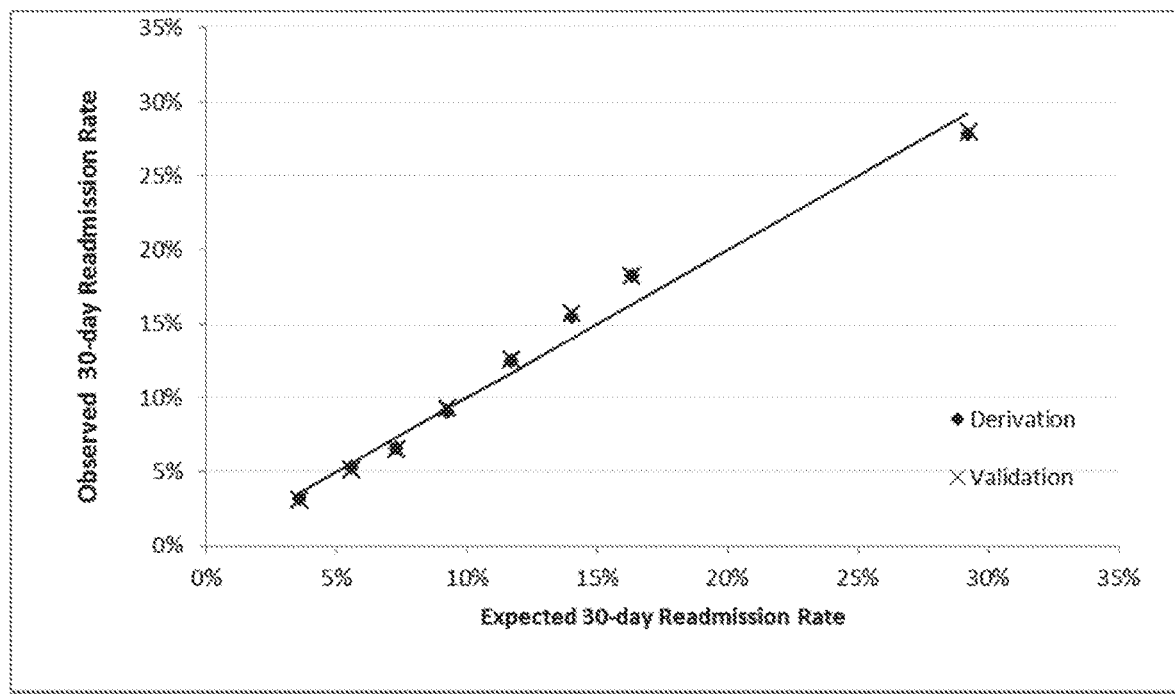
FIG. 9 illustrates an example graph of Hosmer-Lemeshow calibration by derivation and validation cohorts.

For this example, as shown in FIG. 6, the early readmission model yielded a graded relationship of the ALaRMS score 610 and the elevated risk of readmission as shown by the readmission risk score (RRS) 650. Compared with those with an ALaRMS score 610 of ≤10, those with an ALaRMS score 610 between 11 and 20 would have a 53% increase in risk of readmission (odds ratio 620 [OR]: 1.53, 95% confidence intervals 630 [CI]: 1.47, 1.60). In general, the higher the ALaRMS score 610, the higher the readmission risk (e.g., RRS score 630). Also, the number of discharges during the previous 90 days was a significant predictor of readmission. Compared to those with no hospital discharges in the previous 90 days, a single previous discharge would double the risk of readmission (OR 620: 2.08 [CI 630: 2.05, 2.12). The more frequent previous discharges, the higher the readmission risk. This early readmission risk model had a c-statistic 710 of 0.69 (FIG. 7). The Hosmer-Lemeshow goodness-of-fit test indicated good calibration for both derivation and validation cohorts 310, 320 (FIG. 9).

Figure 10:
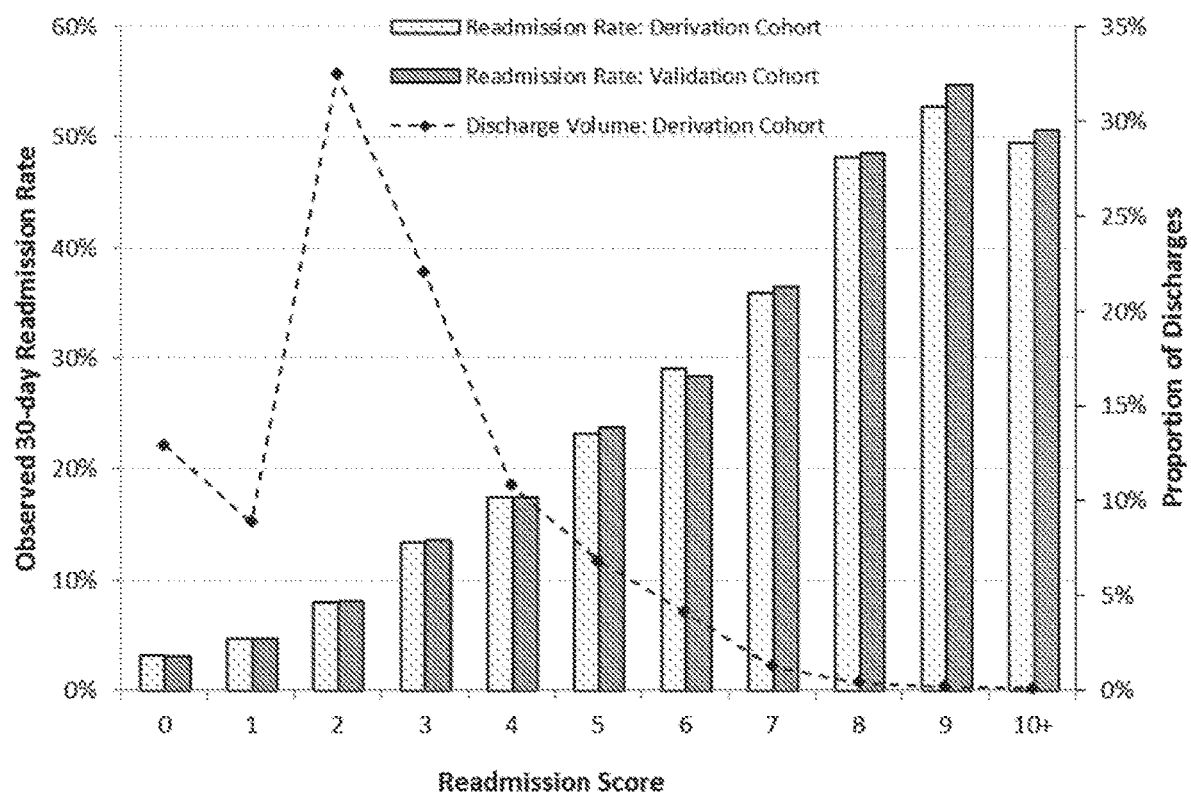
FIG. 10 illustrates an example graph of early readmission risk score (RRS) distribution.

The RRS 650 prevalence distribution and corresponding readmission rates by derivation and validation cohorts 310, 320 are shown in FIG. 10. There were 12.9% discharges falling into the lowest RRS 650 group (RRS=0), whose readmission rate was 3.2%. In contrast, for those in the top two highest RRS 650 groups (RRS=9 or 10+), over 50% were readmitted. With each point increase of RRS 650, there was a nearly a linear increase of readmission risk. The Cochran-Armitage trending test was significant (P<0.0001).

The sensitivity analysis revealed that the RRS 650 model had similar predictive power for the patient populations in the teaching versus non-teaching, small versus large, or rural versus urban hospitals, with a c-statistic 710 ranging from 0.690 to 0.706 (FIG. 8). It also displayed a similar c-statistic 710 for medical versus surgical patients (0.692 versus 0.690). When patients were segregated into subgroups by major disease categories, 14 out of 17 (82%) categories had a c-statistic 710 above 0.65, 2 (12%) between 0.60 and 0.64, only 1 category (complications of pregnancy, childbirth, and the puerperium) was below 0.60 due to very low readmission rate of 2.9%.

For one or more embodiments, a 30-day readmission risk score may be used for adult patients admitted to acute care hospitals based on objective clinical parameters available at the time of hospital admission. This is the largest (over one million discharges) clinical database consisting of laboratory test results used for readmission model development and validation. The large sample size resulted in a more precise risk estimate as evidence by the tight confidence intervals of risk factors. A graded relationship between the RRS 650 and the readmission may be determined. In one example, the validity of this RRS 650 may be tested prospectively in an environment with electronic healthcare data automation. Further, this scoring system may be used for prioritizing discharge planning and coordinating care transition and management early in the hospital stay. Given the average hospital length of stay (LOS) is approximately 3-4 days, identifying patients with high readmission risk at the early hospital stay provides pragmatic value. In one or more embodiments, the readmission risk or RRS 650 may be determined for any day other than the day of admission, for a patient visit to an outpatient or ambulatory care facility, for a patient visit to a rehabilitation facility or for in-home patient care, for example.

The objective nature of the determined RRS 650 without discharge diagnosis-based variables has the c-statistic 710 of 0.69, which is comparable with 0.69 reported for readmission models for all patients that used both clinical and diagnosis-based comorbidity data. When discharge diagnosis based variables were added, the model discrimination (c-statistic 710) increased from 0.69 to 0.73. The post-discharge model may serve as a retrospective risk adjustment tool for hospital comparisons and outcome research. When the model is applied to the three disease groups being reported by the CMS, the c-statistics 710 of the resulting models were higher than the CMS readmission models: 0.63 vs 0.60 (CHF), 0.65 vs. 0.63 (AMI), 0.68 vs 0.63 (pneumonia), respectively, albeit the definition of disease groups and patient population may not be directly comparable. In more recent CMS efforts using administrative data alone to predict 30-day all-cause readmissions hospital-wide, the reported model c-statistics 710 ranged from 0.604 to 0.676, which are lower than the determined model and other reported models using both clinical and administrative data. Perhaps more importantly, incorporating objective clinical data increases the clinical plausibility.

Many factors affect readmission, where some are intrinsic. With disease progression, a patient's physiologic reserve weakens and the clinical condition deteriorates to the point where the need for more frequent acute care becomes necessary. The more physiologic reserves are depleted, the more likely the readmission. This depletion can be objectively assessed by the laboratory test results and other clinical parameter. Thus, the finding that the ALaRMS score 610, which consists of age, gender, and abnormal laboratory test results, was correlated in a graded fashion with readmission risk (RRS 650) demonstrates that patients' physiologic reserve and clinical severity play an important role in re-hospitalization. The 23 numeric laboratory results assessed the functions of major organ systems needed for survival. The further the deviation from the reference range, the more severe the clinical conditions. Thus, incorporating laboratory data in the readmission model may provide advantages. For example, they are objective and less prone to variations in subjective judgment. As another example, they are quantitative, allowing more accurate depiction of graded relationship of severity and the outcome. As a further example, they are widely automated in the EHR system, allowing potential automated application of algorithms.

The finding that number of admissions during the previous three months is a strong predictor of reemission is plausible, given that the more frequent hospitalization may potentially reflects disease progression, continued physiologic decline, or near the end of life. This is consistent with previous studies.

For retrospectively collected post-discharge administrative data, principal diagnosis-based disease group variables 720 may enhance the model discrimination. Certain clinical conditions are more likely to require re-hospitalization than others. For example, severe systemic or chronic diseases affecting major organ systems such as infections, neoplasms, circulatory, respiratory, endocrine, or other systems might be more likely to be associated with readmissions. Hence, adding the principal diagnosis-based disease groups improves model discrimination. Other variables from administrative data, such as secondary diagnosis-based comorbidity scores 730, added a small improvement (from 0.725 to 0.732) above and beyond what have been in the model. The small impact of comorbidity may be due to the objective assessment of physiological function by the clinical laboratory data that have already accounted for comorbidity to a large extent. This finding is consistent with a previous study that found limited contribution of comorbidity when clinical data are used in the model. Since administrative variables are available after patients are discharged, the enhanced model may be used for retrospective hospital comparison and outcome research. For example, the administrative data used may be standard billing data, which require no additional data collection cost.

All-cause readmission within 30 days may be used as the outcome without attempting to differentiate avoidable versus non-avoidable readmission. "Avoidable" readmission is difficult to define. For example, an ICD-10 code based system (e.g., SQLape) attempting to identify avoidable readmissions has been developed and used in Switzerland, but it has not been validated in the United States. Some studies have found that the "avoidable" readmission rates range was 5.0%-78.9%. The large range may indicate partially the variation of the definition of "avoidable" readmission.

In some embodiments, the conceptualization builds on the assumption that with the disease progression, patients' physiological reserves weakens, which increases probability of readmission. Hence, certain admission rates may be determined based on the weight of a given patient population with risk factors identified in the model. Hospitals and healthcare systems with more efficient transition planning or other follow-up preventive interventions may reduce the probability of readmissions and hence, lower risk standardized readmission rates (e.g., better performance). Adjusting physiological severity and primary diseases of major organ system may be more practical and fair than trying to define "avoidable" consistently in terms of implementing a hospital comparison metric.

In an example, the study patient population comprised consecutive patients from over 70 hospitals. Although this is an improvement from a single center study in terms of patient diversity, it may still not be representative of the US patient population. Some studies have found socioeconomic status (SES) as being a risk factor for readmission. This may be assessed using Medicaid as a surrogate, which added a 0.006 to the c-statistic 710 (from 0.692 to 0.698) above the RRS 650 model for this example. This small improvement in discrimination was in line with other studies which have found either little or no improvement in the model discrimination. However, there is a controversy regarding the use of SES as a risk adjuster for hospital comparison purposes because of the concern that the higher readmission of the low SES patients may be associated with lower quality of care provided to the disadvantaged patient population.

Unlike predicting the mortality risk, which showed highly accurate predictive power when objective clinical data are carefully crafted, predicting readmission remains complex. In addition to the intrinsic clinical risk of the patients which can be measured objectively, extrinsic risk factors, including social and environmental factors may play important roles. The external risk factors can be difficult to collect electronically and accurately after patients are discharged without integrated healthcare systems.

For the purpose of risk adjusted public reporting metrics, it may not even be desirable to adjust for process variables that are under the control of care providers. If a substandard care process, such as poor care coordination, is associated with higher readmission rate, then adding these variables in the model would give more credit (expecting more readmissions) to those hospitals/systems doing a lesser job than those who do a better job in coordinating care. Nevertheless, with increasing automation and connectivity of the healthcare system, factors that influence readmissions, such as discharge transition, post discharge care, social support, might be captured electronically and studied to enhance the care system and reduce readmissions.

Accordingly, automated clinical laboratory data may be used to generate a readmission risk score early at hospital admission with fair discrimination. A readmission risk score may be implemented and tested in an electronic health care system to aid early care transition planning. A post-discharge model adding post-discharge diagnosis data may enhance readmission predictive accuracy. The enhanced post-discharge model may be used for risk adjusted hospital comparison and outcome research.

In one or more embodiments, a patient's RRS 650 may be determined and then attached to one or more patient testing or treatment processes. For example, upon admission to a hospital, a patient's RRS 650 may be determined and added to all of the laboratory test orders and medication dispensing orders prescribed for the patient's care. For each process, the patient's RRS 650 may dictate additional testing or medication, or a different testing or treatment protocol. Conversely, data from the administration of the test or treatment to the patient may be utilized to determine a revised RRS 650, such that the revised RRS 650 is attached to any further test or treatment orders. For example, the patient may undergo three different test procedures and receive two different treatments in a particular period of time, with the patient's RRS 650 being dynamically re-determined after the administration of each test or treatment. In such a case, for example, the three test procedures may cause the patient's RRS 650 to change such that one of the prescribed medications is no longer necessary to be administered to the patient or an additional medication is added in order to minimize the likelihood that the patient will need to be readmitted to the hospital. Also, the RRS 650 improves the functioning of the medical device 80 with respect to the testing or treatment of the patient. Further, the RRS 650 improves the efficiency of the control system 40 because having a stored RRS 650 for a particular patient allows the control system 40 to quickly and efficiently provide operating parameters for configuration of the medical device 80.

Figure 11:
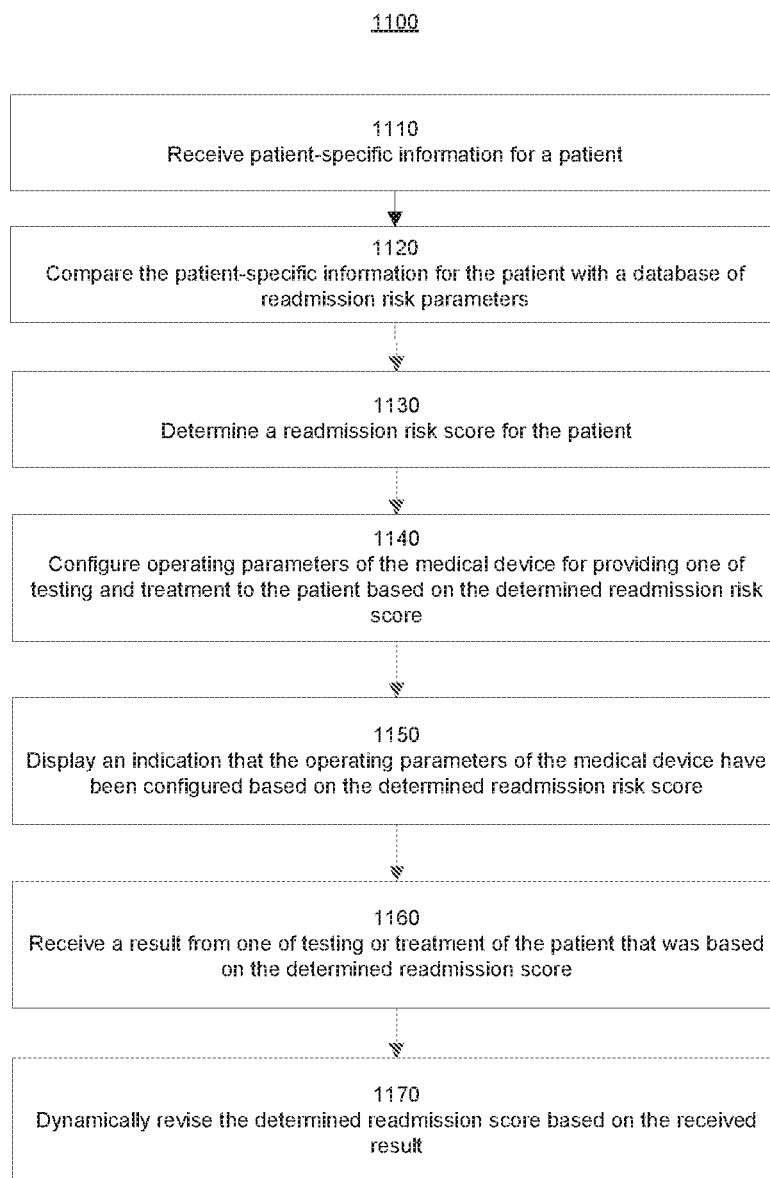
FIG. 11 illustrates a flow diagram of an example process for reducing medical facility readmission risk.

FIG. 11 illustrates a method of determining and using a readmission risk score 1100. In step 1110, patient-specific information is received or determined as it pertains to a patient. The patient-specific information is compared to a database of readmission risk parameters in step 1120. In step 1130, a readmission risk score for is determined for the patient, the readmission risk score indicating the risk that the patient will have to be readmitted to the hospital or other health care facility. In step 1140, a medical device for providing a medical test on the patient or medical treatment to the patient is configured based on the determined readmission risk score for that patient. An indication that the medical device has been configured based on the determined readmission risk score for that patient is displayed on the medical device in step 1150. In step 1160, a test result or medication treatment result related to the patient is received. In step 1170, the readmission risk score of the patient is dynamically revised based on the received test result.

Figure 12:
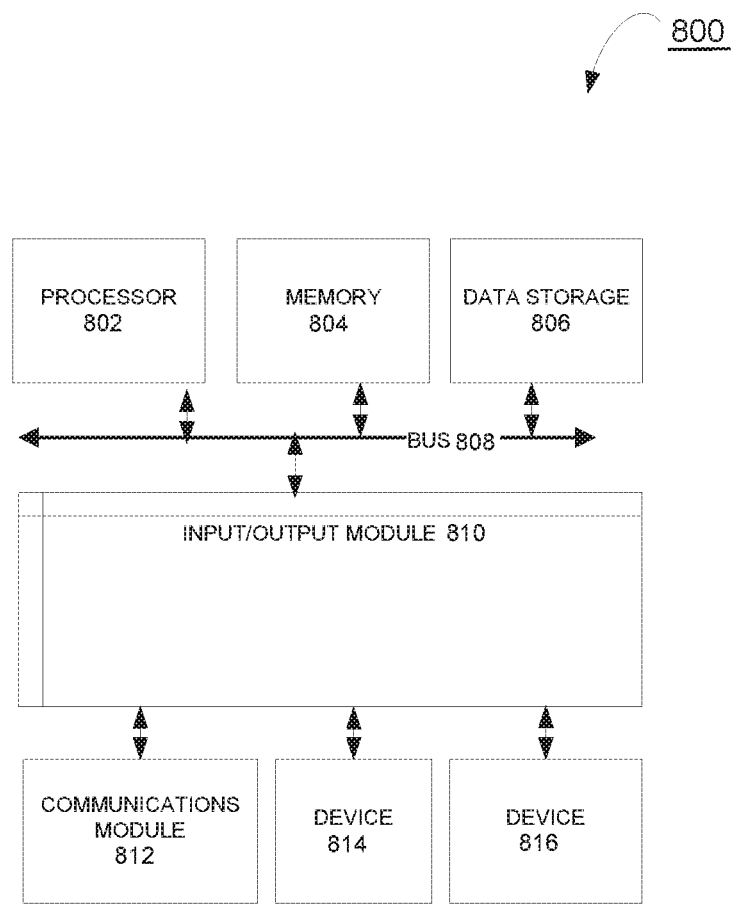
FIG. 12 conceptually illustrates an electronic system with which one or more embodiments of the subject technology may be implemented.

FIG. 12 conceptually illustrates electronic system 800 with which one or more embodiments of the subject technology may be implemented. Electronic system 800, for example, can be a server 110, 120, a desktop computer, a laptop computer, a tablet computer, a phone, a personal digital assistant (PDA), and the like. Such an electronic system includes various types of computer readable media and interfaces for various other types of computer readable media. Electronic system 800 includes bus 808, processing unit(s) 812, system memory 804, read-only memory (ROM) 810, permanent storage device 802, input device interface 814, output device interface 806, and network interface 816, or subsets and variations thereof.

Bus 808 collectively represents all system, peripheral, and chipset buses that communicatively connect the numerous internal devices of electronic system 800. In one or more embodiments, bus 808 communicatively connects processing unit(s) 812 with ROM 810, system memory 804, and permanent storage device 802. From these various memory units, processing unit(s) 812 retrieves instructions to execute and data to process in order to execute the processes of the subject disclosure. The processing unit(s) can be a single processor or a multi-core processor in different embodiments.

ROM 810 stores static data and instructions that are needed by processing unit(s) 812 and other modules of the electronic system. Permanent storage device 802, on the other hand, is a read-and-write memory device. This device is a non-volatile memory unit that stores instructions and data even when electronic system 800 is off. One or more embodiments of the subject disclosure use a mass-storage device (such as a magnetic or optical disk and its corresponding disk drive) as permanent storage device 802.

Other embodiments use a removable storage device (such as a flash drive) as permanent storage device 802. Like permanent storage device 802, system memory 804 is a read-and-write memory device. However, unlike storage device 802, system memory 804 is a volatile read-and-write memory, such as random access memory. System memory 804 stores any of the instructions and data that processing unit(s) 812 needs at runtime. In one or more embodiments, the processes of the subject disclosure are stored in system memory 804, permanent storage device 802, and/or ROM 810. From these various memory units, processing unit(s) 812 retrieves instructions to execute and data to process in order to execute the processes of one or more embodiments.

Bus 808 also connects to input and output device interfaces 814 and 806. Input device interface 814 enables a user to communicate information and select commands to the electronic system. Input devices used with input device interface 814 include, for example, alphanumeric keyboards and pointing devices (also called "cursor control devices"). Output device interface 806 enables, for example, the display of images generated by electronic system 800. Output devices used with output device interface 806 include, for example, printers and display devices, such as a liquid crystal display (LCD), a light emitting diode (LED) display, an organic light emitting diode (OLED) display, a flexible display, a flat panel display, a solid state display, a projector, or any other device for outputting information. One or more embodiments may include devices that function as both input and output devices, such as a touchscreen. In these embodiments, feedback provided to the user can be any form of sensory feedback, such as visual feedback, auditory feedback, or tactile feedback; and input from the user can be received in any form, including acoustic, speech, or tactile input.

Also as shown in FIG. 12, bus 808 also couples electronic system 800 to a network (not shown) through network interface 816. In this manner, the computer can be a part of a network of computers (such as a local area network ("LAN"), a wide area network ("WAN"), or an Intranet, or a network of networks, such as the Internet. Any or all components of electronic system 800 can be used in conjunction with the subject disclosure.

In one or more embodiments a system is provided for reducing medical facility readmission risk, the system including a medical device that is configurable with operating parameters for providing one of testing and treatment to a patient and a medical control system. The medical control system includes a memory comprising patient-specific information for the patient and a readmission risk database comprising readmission risk parameters and a processor. The processor is configured to compare the patient-specific information for the patient with the readmission risk parameters; determine a readmission risk score for the patient; receive a patient protocol based on decision support provided by the determined readmission risk score; and provide a configuration of the operating parameters of the medical device for providing the one of testing and treatment to the patient based on the received patient protocol.

In one or more embodiments the processor is further configured to provide a notification for display by the medical device indicating that the operating parameters of the medical device have been configured based on the received patient protocol, the notification comprising information regarding the configured operating parameters. In one or more embodiments the determination of a readmission risk score may include any of: providing an early readmission risk model based on a derivation cohort; validating the early readmission risk model with a validation cohort; determining demographic information of the patient, the demographic information comprising at least one of the patient's age, the patients gender, and the patient's ethnicity; to determine at least one laboratory test result for the patient; to determine a number of health facility discharges for the patient over a predetermined period of time; and to determine the method of payment for the patient. In one or more embodiments the determination of a readmission risk score is based at least partially on a principal diagnosis-based clinical classification system. In one or more embodiments the determination of a readmission risk score is based at least partially on a secondary diagnosis-based comorbidity score. In one or more embodiments the processor is further configured to: store the determined readmission risk score in the readmission risk database; receive a result from one of testing or treatment of the patient that was based on the determined readmission risk score; dynamically revise the determined readmission risk score based on the received result; and store the dynamically revised readmission risk score in the readmission risk database. In one or more embodiments the processor is further configured to: receive a revised protocol based on decision support provided by the dynamically revised readmission risk score; and modify the configuration of the operating parameters of the medical device for providing the one of testing and treatment to the patient based on the revised protocol.

In one or more embodiments a method for use with a medical device for reducing medical facility readmission risk, the method including: determining patient-specific information for a patient; comparing the patient-specific information for the patient with a database of readmission risk parameters; determining a readmission risk score for the patient; determining a patient protocol for the patient based on decision support provided by the determined readmission risk score; configuring, by a processor of the medical device, operating parameters of the medical device for providing one of testing and treatment to the patient based on the determined patient protocol; and displaying, by the medical device, an indication that the operating parameters of the medical device have been configured based on the determined patient protocol, the notification comprising information regarding the configured operating parameters.

In one or more embodiments the determining the readmission risk score comprises: providing an early readmission risk model based on a derivation cohort; and validating the early readmission risk model with a validation cohort. In one or more embodiments the determining the readmission risk score comprises at least one of: determining demographic information of the patient; determining at least one laboratory test result for the patient; and determining a number of health facility discharges for the patient over a predetermined period of time. In one or more embodiments the determining the readmission risk score is based on at least one of: a principal diagnosis-based clinical classification system; and a secondary diagnosis-based comorbidity score. In one or more embodiments the method further comprises: storing the determined readmission risk score in the readmission risk database; receiving a result from one of testing or treatment of the patient; dynamically revising the determined readmission risk score based on the received result; and storing the dynamically revised readmission risk score in the readmission risk database. In one or more embodiments the method further comprises: receiving a revised patient protocol based on decision support provided by the dynamically revised readmission risk score; and modifying the configuration of the operating parameters of the medical device for providing the one of testing and treatment to the patient based on the revised patient protocol.

In one or more embodiments a non-transitory machine-readable medium is provided that embodies instructions that, when executed by a machine, cause the machine to perform a method for determining a readmission risk score. The method includes receiving patient-specific information for a patient; comparing the received patient-specific information for the patient with a database of readmission risk parameters; determining a readmission risk score for the patient; storing the patient's determined readmission risk score; determining a patient protocol for the patient based on decision support provided by the stored readmission risk score; configuring, by the machine, operating parameters of the medical device for providing one of testing and treatment to the patient based on the determined patient protocol; and displaying, by the medical device, an indication that the operating parameters of the medical device have been configured based on the determined patient protocol, the notification comprising information regarding the configured operating parameters.

In one or more embodiments the method further comprises: dynamically revising the patient's stored readmission risk score based on a result from one of testing or treatment of the patient; receiving a revised patient protocol based on decision support provided by the dynamically revised readmission risk score; and configuring, by the machine, operating parameters of another medical device for providing one of testing and treatment to the patient based on the revised patient protocol.

Many of the above-described features and applications may be implemented as software processes that are specified as a set of instructions recorded on a computer readable storage medium (alternatively referred to as computer-readable media, machine-readable media, or machine-readable storage media). When these instructions are executed by one or more processing unit(s) (e.g., one or more processors, cores of processors, or other processing units), they cause the processing unit(s) to perform the actions indicated in the instructions. Examples of computer readable media include, but are not limited to, RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, ultra density optical discs, any other optical or magnetic media, and floppy disks. In one or more embodiments, the computer readable media does not include carrier waves and electronic signals passing wirelessly or over wired connections, or any other ephemeral signals. For example, the computer readable media may be entirely restricted to tangible, physical objects that store information in a form that is readable by a computer. In one or more embodiments, the computer readable media is non-transitory computer readable media, computer readable storage media, machine readable media, or machine readable storage media.

In one or more embodiments, a computer program product (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

While the above discussion primarily refers to microprocessor or multi-core processors that execute software, one or more embodiments are performed by one or more integrated circuits, such as application specific integrated circuits (ASICs) or field programmable gate arrays (FPGAs). In one or more embodiments, such integrated circuits execute instructions that are stored on the circuit itself.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that any specific order or hierarchy of blocks in the processes disclosed is an illustration of example approaches. Based upon design preferences, it is understood that the specific order or hierarchy of blocks in the processes may be rearranged, or that all illustrated blocks be performed. Any of the blocks may be performed simultaneously. In one or more embodiments, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The predicate words "configured to," "operable to," and "programmed to" do not imply any particular tangible or intangible modification of a subject, but, rather, are intended to be used interchangeably. In one or more embodiments, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as an "aspect" may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as a "configuration" may refer to one or more configurations and vice versa.

The word "exemplary" is used herein to mean "serving as an example, instance, or illustration." Any embodiment described herein as "exemplary" or as an "example" is not necessarily to be construed as preferred or advantageous over other embodiments. Also, to the extent that the term "include," "have," or the like is used in the description or the claims, such term is intended to be inclusive in a manner similar to the term "comprise" as "comprise" is interpreted when employed as a transitional word in a claim. Furthermore, to the extent that the term "include," "have," or the like is used in the description or the claims, such term is intended to be inclusive in a manner similar to the term "comprise" as "comprise" is interpreted when employed as a transitional word in a claim.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

Reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other variations are within the scope of the following claims.

What is claimed is:

1. A system for use with a medical device for reducing medical facility readmission risk, the system comprising:
    a medical device that is configurable with operating parameters for providing one of testing and treatment to a patient; and
    a medical control system comprising:
        a memory comprising patient-specific information for the patient and a readmission risk database comprising readmission risk parameters;
        a processor configured to:
            compare the patient-specific information for the patient with the readmission risk parameters;
            determine a readmission risk score for the patient;
            receive a patient protocol based on decision support provided by the determined readmission risk score;
            provide a configuration of the operating parameters of the medical device for providing the one of testing and treatment to the patient based on the received patient protocol; and automatically inhibit the medical device from starting administration of the testing or treatment to the patient if the readmission risk score for the patient indicates that one or more of the patient-specific information and the readmission risk parameters do not meet institutionally established guidelines for decreasing the risk of hospital readmission for the patient, wherein the determination of a readmission risk score comprises to determine a number of health facility discharges per patient over a predetermined period of time.

2. The system of claim 1, wherein the processor is further configured to:

provide a notification for display by the medical device indicating that the operating parameters of the medical device have been configured based on the received patient protocol, the notification comprising information regarding the configured operating parameters.

3. The system of claim 1, wherein the determination of a readmission risk score comprises:

to provide an early readmission risk model based on a derivation cohort.

4. The system of claim 3, wherein the determination of a readmission risk score further comprises:

to validate the early readmission risk model with a validation cohort.

5. The system of claim 1, wherein the determination of a readmission risk score comprises:

to determine demographic information of the patient, the demographic information comprising at least one of the patient's age, the patients gender, and the patient's ethnicity.

6. The system of claim 1, wherein the determination of a readmission risk score comprises:

to determine at least one laboratory test result for the patient.

7. The system of claim 1, wherein the determination of a readmission risk score comprises:

to determine the method of payment for the patient.

8. The system of claim 1, wherein the determination of a readmission risk score is based at least partially on a principal diagnosis-based clinical classification system.

9. The system of claim 1, wherein the determination of a readmission risk score is based at least partially on a secondary diagnosis-based comorbidity score.

10. The system of claim 1, wherein the processor is further configured to:

store the determined readmission risk score in the readmission risk database;

receive a result from one of testing or treatment of the patient that was based on the determined readmission risk score;

dynamically revise the determined readmission risk score based on the received result; and store the dynamically revised readmission risk score in the readmission risk database.

11. The system of claim 10, wherein the processor is further configured to:

receive a revised protocol based on decision support provided by the dynamically revised readmission risk score; and modify the configuration of the operating parameters of the medical device for providing the one of testing and treatment to the patient based on the revised protocol.

12. The system of claim 1, wherein the processor is further configured to one of cause the medical device to display an alert and require a confirmation step, based on one of a care area in which the medical device is located and the level of experience of a caregiver associated with the medical device.

13. A method for use with a medical device for reducing medical facility readmission risk, the method comprising:

determining patient-specific information for a patient;

comparing the patient-specific information for the patient with a database of readmission risk parameters;

determining a readmission risk score for the patient;

determining a patient protocol for the patient based on decision support provided by the determined readmission risk score;

configuring, by a processor of the medical device, operating parameters of the medical device for providing one of testing and treatment to the patient based on the determined patient protocol;

displaying, by the medical device, an indication that the operating parameters of the medical device have been configured based on the determined patient protocol, the notification comprising information regarding the configured operating parameters; and automatically inhibiting the medical device from starting administration of the testing or treatment to the patient if the readmission risk score for the patient indicates that one or more of the patient-specific information and the readmission risk parameters do not meet institutionally established guidelines for decreasing the risk of hospital readmission for the patient, wherein the determining a readmission risk score comprises determining a number of health facility discharges per patient over a predetermined period of time.

14. The method of claim 13, wherein the determining the readmission risk score comprises:

providing an early readmission risk model based on a derivation cohort; and validating the early readmission risk model with a validation cohort.

15. The method of claim 13, wherein the determining the readmission risk score comprises at least one of:

determining demographic information of the patient; and determining at least one laboratory test result for the patient.

16. The method of claim 13, wherein the determining the readmission risk score is based on at least one of:

a principal diagnosis-based clinical classification system; and a secondary diagnosis-based comorbidity score.

17. The method of claim 13, further comprising:

storing the determined readmission risk score in the readmission risk database;

receiving a result from one of testing or treatment of the patient;

dynamically revising the determined readmission risk score based on the received result; and storing the dynamically revised readmission risk score in the readmission risk database.

18. The method of claim 17, further comprising:

receiving a revised patient protocol based on decision support provided by the dynamically revised readmission risk score; and modifying the configuration of the operating parameters of the medical device for providing the one of testing and treatment to the patient based on the revised patient protocol.

19. A non-transitory machine-readable medium embodying instructions that, when executed by a machine, cause the machine to perform a method for determining a readmission risk score, the method comprising:
receiving patient-specific information for a patient;
comparing the received patient-specific information for the patient with a database of readmission risk parameters;
determining a readmission risk score for the patient;
storing the patient's determined readmission risk score;
determining a patient protocol for the patient based on decision support provided by the stored readmission risk score;
configuring, by the machine, operating parameters of the medical device for providing one of testing and treatment to the patient based on the determined patient protocol;
displaying, by the medical device, an indication that the operating parameters of the medical device have been configured based on the determined patient protocol, the notification comprising information regarding the configured operating parameters; and
automatically inhibiting the medical device from starting administration of the testing or treatment to the patient if the readmission risk score for the patient indicates that one or more of the patient-specific information and the readmission risk parameters do not meet institutionally established guidelines for decreasing the risk of hospital readmission for the patient,
wherein the determining a readmission risk score comprises determining a number of health facility discharges per patient over a predetermined period of time.

20. The non-transitory machine-readable medium of claim 19, wherein the method further comprises:
dynamically revising the patient's stored readmission risk score based on a result from one of testing or treatment of the patient;
receiving a revised patient protocol based on decision support provided by the dynamically revised readmission risk score; and
configuring, by the machine, operating parameters of another medical device for providing one of testing and treatment to the patient based on the revised patient protocol.

\* \* \* \* \*